United States Patent [19]

Fewster

[11] Patent Number: 5,748,509

[45] Date of Patent: May 5, 1998

[54] ANALYSING A MATERIAL SAMPLE

[75] Inventor: Paul F. Fewster, Brighton, England

[73] Assignee: U.S. Philips Corporation, New York, N.Y.

[21] Appl. No.: 495,054

[22] Filed: Jun. 26, 1995

[30] Foreign Application Priority Data

Jun. 25, 1994 [GB] United Kingdom ............... 9412839
Jan. 19, 1995 [GB] United Kingdom ............... 9500999

[51] Int. Cl.$^6$ ............................................. G06F 15/20
[52] U.S. Cl. ...................... 364/578; 364/485; 364/498; 73/800; 378/70
[58] Field of Search .................... 364/498, 485; 395/500; 73/800; 378/70

[56] References Cited

U.S. PATENT DOCUMENTS

| | | | |
|---|---|---|---|
| 5,154,795 | 10/1992 | Ishida et al. | 156/601 |
| 5,299,138 | 3/1994 | Fiori et al. | 364/498 |
| 5,442,676 | 8/1995 | Fewster | 378/72 |
| 5,488,476 | 1/1996 | Mansfield et al. | 356/354 |
| 5,546,811 | 8/1996 | Rogers et al. | 73/800 |
| 5,583,780 | 12/1996 | Kee et al. | 364/468.24 |

FOREIGN PATENT DOCUMENTS 0110469  6/1984  European Pat. Off. ............ 364/578

OTHER PUBLICATIONS

"A High-Resolution Multiple-Crystal Multiple-Reflection Diffractometer" by Paul F. Fewster, J. Appl. Cryst. (1989) 22, pp. 64–69.

Primary Examiner—Kevin J. Teska
Assistant Examiner—A. S. Roberts

[57] ABSTRACT

A computer system (1) has a data base (DB1) of analytical procedures (AP) for analysing a material sample (30) using radiation such as X-ray radiation. The computer system requests a user to input to the system (1) information for identifying at least one desired parameter ($P_d$) of the material sample (30). The computer system (1) uses this information to identify the possible analytical procedures for determining that desired parameter. An analytical procedure or procedures selected by the user and/or computer system is then simulated by the computer system to produce a first simulation ($I_1$) of radiation leaving the sample. The selected analytical procedure is simulated again after the computer system has varied the influence of the desired parameter ($P_d$) to produce a second simulation ($I_2$). The computer system then compares the first and second simulations ($I_1$ and $I_2$) to determine where the difference between the first and second simulations is greatest so as to enable an experiment to be conducted in the area or areas most sensitive to the desired parameter.

20 Claims, 4 Drawing Sheets

ANALYSING A MATERIAL SAMPLE

BACKGROUND OF THE INVENTION

1. Field of the Invention

This invention relates to methods and apparatus for use in analysing a material sample using radiation, and involves the use of a computer-based knowledge system.

2. Description of the Related Art

Conventionally, when a person wishes to carry out an experiment, for example an X-ray diffraction experiment, to determine desired parameters or information about a material sample using radiation, it is necessary for the user or experimenter to rely on his own knowledge or the knowledge of colleagues to design the experiment and accordingly the accuracy and usefulness of the results of the experiment are very much dependent on the knowledge and experience of the experimenter and his colleagues.

SUMMARY OF THE INVENTION

It is an aim of the present invention to enable the provision of a method and apparatus for designing such an experiment and carrying out such an analytical procedure which removes or at least reduces the dependence of the accuracy and usefulness of the results on the experience of the user or experimenter.

According to a first aspect of the present invention, there is provided a method of carrying out an analytical procedure using analytical apparatus having a computer system provided with a data base of analytical procedures for analysing a material sample, in which method the computer system requests a user to input to the computer system information for identifying at least one desired parameter of the material sample which is of interest to the user, determines from the information input by the user which of the analytical procedures in the data base may be used to obtain the desired information, simulates at least one analytical procedure selected from the possible analytical procedures to produce a first simulation of radiation leaving the sample, varies at least one desired parameter of interest to the user, simulates the selected analytical procedure again after having varied the influence of the at least one desired parameter to produce a second simulation of radiation leaving the sample, compares the first and second simulations to determine the area or areas where the difference between the first and second simulations is greatest, and then is used to control the analytical apparatus to cause an experiment to be carried out using the analytical procedure in the area or areas most sensitive to the at least one desired parameter.

According to a second aspect of the present invention, there is provided a method for designing an experiment for analysing a material sample using radiation, which method involves the use of a computer system having a data base of analytical procedures for analysing a material sample by causing radiation to be incident on the sample and detecting radiation leaving the sample, in which method the computer system requests a user to input to the computer system information for identifying at least one desired parameter of the material sample which is of interest to the user, determines from the information input by the user which of the analytical procedures in the data base may be used to obtain the desired information, simulates at least one analytical procedure selected from the possible analytical procedures to produce a first simulation of radiation leaving the sample, varies at least one desired parameter of interest to the user, simulates the selected analytical procedure again after having varied the influence of the at least one desired parameter to produce a second simulation of radiation leaving the sample, and compares the first and second simulations to determine the area or areas where the difference between the first and second simulations is greatest to enable an experiment to be conducted in the area or areas most sensitive to the at least one desired parameter.

A method in accordance with the invention allows an inexperienced user to set up an appropriate experiment with the assistance of the computer system which effectively forms an expert system storing available information on possible appropriate analytical procedures to enable the analytical procedure most appropriate to the problem in hand to be selected by the user and/or by the computer system. Moreover, by comparing the first and second simulations to take into account the variation of the at least one desired parameter, a method in accordance with the invention enables the area or areas most sensitive to the at least one desired parameter to be determined so that, within the constraints of the experimental set up, the best possible and most accurate value or values for the at least one desired parameter can be obtained. Such a method excels both quantitatively and qualitatively over what could previously be achieved by even an experienced user relying on his own previous knowledge and experience and/or that of other expert sources that he might consult. Thus, in accordance with the invention the choice of the analytical experiment to be conducted can be made from well-defined information about the experiment, its required time and/or its accuracy, this information being derived in a precise manner using simulations and being so derived after consideration of a large number of possible experiments and different analytical procedures and after identifying the area or areas most sensitive to the parameter(s) of interest to the user. A method in accordance with the first aspect of the invention in addition allows the analytical apparatus to be controlled automatically so that an inexperienced user does not need to be advised how to set up the analytical apparatus.

It should be understood that, as used herein, the term "radiation" includes any electromagnetic radiation such as X-ray, gamma, visible, infra-red or ultra-violet electromagnetic radiation or any particle radiation such as electron or neutron beam radiation.

The computer system may advise of the area or areas most sensitive to the at least one desired parameter to enable the user to carry out the appropriate experiment or experiments, and/or the computer system may use the information to set up automatically the appropriate experiment or experiments on suitable apparatus coupled to the computer system. This latter possibility may be particularly advantageous where the user is inexperienced in setting up the apparatus as required to carry out an experiment.

Conveniently, the analytical procedures in the data base are stored cross-referenced to keywords and the computer system requests the user to input the information for identifying the at least one desired parameter by identifying the relevant keyword or keywords. This should assist the inexperienced user in inputting the correct information into the computer system.

Once the user and/or the computer system has selected an analytical procedure, the computer system may request the user to supply information to enable the values of parameters required to produce the first simulation to be determined. This may make use of a further data base or further data bases of known parameters for known elements and material compounds from which the values of parameters required to produce the first simulation may be determined.

If all of the required parameters for producing the first simulation cannot be determined, the computer system may determine, for each unknown parameter, whether the unknown parameter is a primary parameter whose value must be known or a secondary parameter for which an estimate can be used and, where the unknown parameter is a primary parameter, the computer system may determine from the data base of analytical procedures any possible analytical procedure for determining the unknown primary and advise the user of the analytical procedure for determining the unknown primary parameter. This enables the analytical procedure selected for determining the at least one desired parameter to be simulated even if one of the primary parameters is unknown, if a preliminary analytical procedure is available to simulate the unknown primary parameter, and it also allows the user to be guided as to the preliminary experiments required to be carried out before he can carry out the experiment to determine the at least one desired parameter.

Alternatively or additionally, where the unknown parameter is a primary parameter, the computer system may determine from the data base of analytical procedures whether there is any analytical procedure in the data base which can determine the at least one desired parameter but which does not require the unknown parameter as a primary parameter and may advise the user of any such other possible new analytical procedure and then request the user to select a new analytical procedure. This latter possibility enables the user to select, if possible, another procedure which avoids the need for the unknown primary parameter.

Of course, the computer system may adopt both of these approaches and may, for example, only suggest the use of a preliminary analytical procedure to determine the unknown primary parameter if there are no analytical procedures available which can determine the at least one desired parameter without having to use the unknown parameter as a primary parameter. If an unknown parameter is a secondary parameter, the user may be requested to estimate a value or range for the unknown secondary parameter. Alternatively, the computer system may suggest an estimated range or value for the unknown secondary parameter.

A data base of instrument profiles for a number of different apparatus may be provided. The results of the simulations, that is generally either the first and second simulations independently or the results of the comparison of the first and second simulations may then be convoluted with the selected instrument profile to determine the effect of the apparatus on the experiment. Where more than one diffractometer is available to the user, then the user may input information for more than one apparatus and the computer system may then select for each apparatus an instrument profile from the data base of instrument profiles using the information supplied by the user and convolute the results of the simulations with the selected instrument profile for each apparatus to determine the effect of that apparatus on the experiment, and then advise the user of the most appropriate apparatus to use for the experiment. This enables the effect of the actual apparatus to be simulated so that the user can be advised of its effect on the experiment. Where an instrument profile for a particular apparatus is not available, the computer system may instruct the user to carry out a particular experiment or experiments to enable the required characteristics of the apparatus to be determined, which characteristics may be stored as a new instrument profile in the instrument profile data base, for possible future use.

The present invention also provides apparatus for use in a method in accordance with the first or second aspect, comprising a radiation source, means for defining the radiation beam from the source, a sample support for enabling the sample to be oriented in a desired manner relative to the beam, means for defining radiation from the sample mounted to the sample support and a radiation detector for detecting the radiation from the sample mounted to the sample support.

Means may be provided for controlling movement or rotation of the components of the apparatus in accordance with the requirements of the analytical procedure selected by the user. The controlling means may comprise the computer system used for determining the analytical procedure, so enabling automatic set up of the suggested experiment.

In another aspect, the present invention provides apparatus for designing an experiment for analysing a material sample using radiation, the apparatus comprising a computer system having a data base of analytical procedures for analysing a material sample by causing radiation to be incident on the sample and detecting radiation leaving the sample, means for requesting a user to input to the computer system information for identifying at least one desired parameter of the material sample which is of interest to the user, means for determining from the information input by the user which of the analytical procedures in the data base may be used to obtain the desired information, means for simulating at least one analytical procedure selected from the possible analytical procedures to produce a first simulation of radiation leaving the sample, means for varying at least one desired parameter of interest to the user, means for simulating the selected analytical procedure again after having varied the influence of the at least one desired parameter to produce a second simulation of radiation leaving the sample, means for comparing the first and second simulations to determine the area or areas where the difference between the first and second simulations is greatest to enable an experiment to be conducted in the area or areas most sensitive to the at least one desired parameter.

In a further aspect, the present invention provides apparatus for carrying out an analytical procedure, the apparatus comprising a radiation source, means for defining the radiation beam from the source, a sample support for enabling the sample to be oriented in a desired manner relative to the beam, means for defining radiation from the sample mounted to the sample support, a radiation detector for detecting the radiation from the sample mounted to the sample support, a computer system provided with a data base of analytical procedures for analysing a material sample, the computer system having means for requesting a user to input to the computer system information for identifying at least one desired parameter of the material sample which is of interest to the user, means for determining from the information input by the user which of the analytical procedures in the data base may be used to obtain the desired information, means for simulating at least one analytical procedure selected from the possible analytical procedures to produce a first simulation of radiation leaving the sample, means for varying at least one desired parameter of interest to the user, means for simulating the selected analytical procedure again after having varied the influence of the at least one desired parameter to produce a second simulation of radiation leaving the sample, means for comparing the first and second simulations to determine the area or areas where the difference between the first and second simulations is greatest and means for controlling the analytical apparatus to cause the analytical procedure to be conducted in the area or areas most sensitive to the at least one desired parameter.

The means for defining the radiation beam from the source may comprise at least one aperture of variable size and means may be provided for enabling the size of the at least one aperture to be varied to meet the requirements of the selected analytical procedure.

BRIEF DESCRIPTION OF THE DRAWING

Embodiments of the present invention will now be described, by way of example, with reference to the accompanying drawings, in which.

It should of course be understood that the drawings are not to scale and that like reference numerals are used throughout text to refer to like parts.

DETAILED DESCRIPTION OF THE PREFERRED EMBODIMENTS

Figure 1:
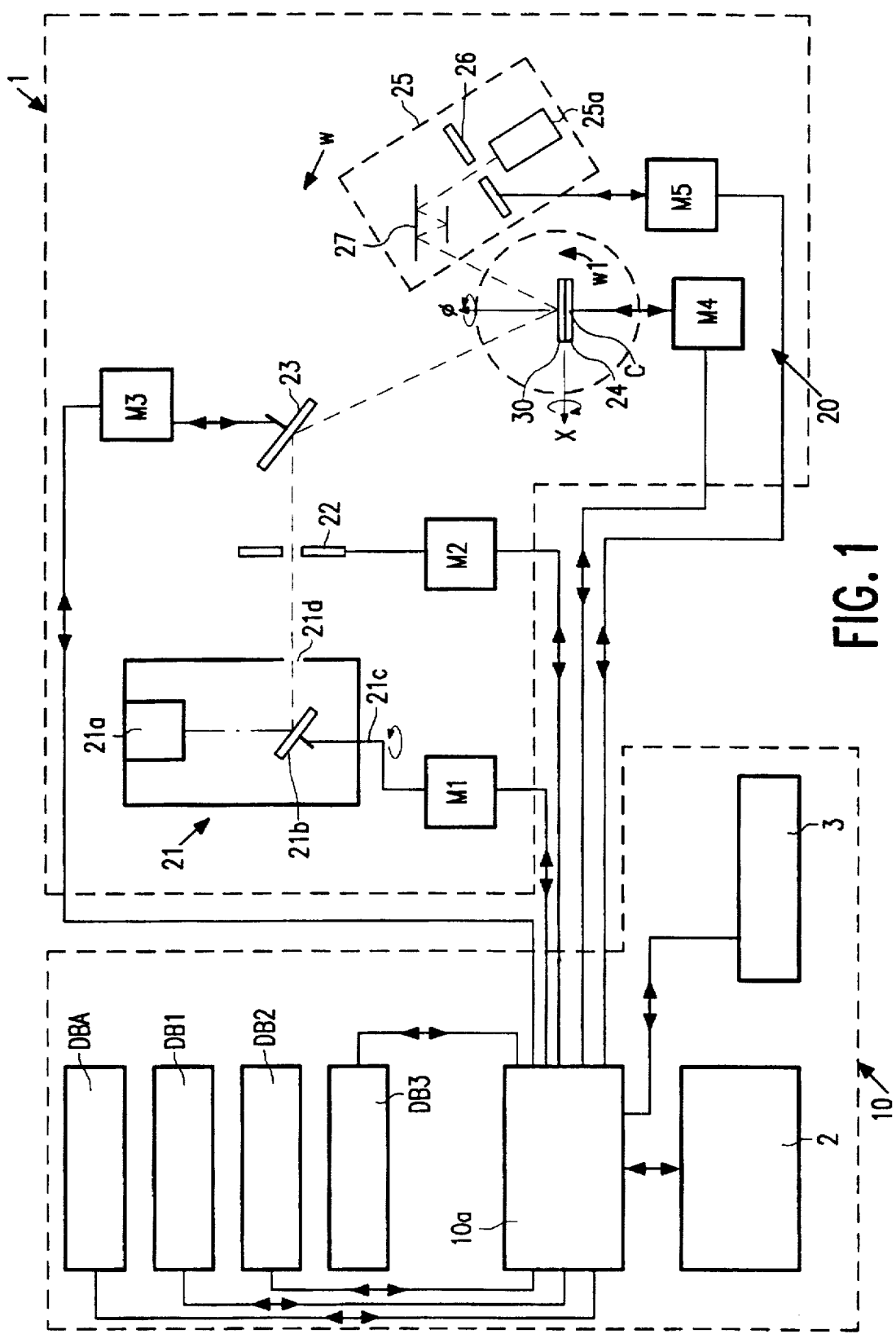
FIG. 1 illustrates diagrammatically apparatus for use in a method in accordance with the invention.

Referring now to the drawings, there is illustrated a method for designing an experiment for analysing a material sample 30 using radiation. The method uses a computer system 10 having a data base DBA of analytical procedures AP for analysing a material sample 30 using radiation, in which the computer system 10 requests a user to input to the computer system 10 information for identifying at least one desired parameter $P_d$ of the material sample 30 which is of interest to the user, determines from the information input by the user which of the analytical procedures AP in the data base DBA may be used to obtain the desired information, may then advise the user of the possible analytical procedures for determining the desired at least one parameter $P_d$, simulates an analytical procedure selected by the user and/or the computer system from the possible analytical procedures to produce a first simulation $I_1$ of radiation leaving the sample, simulates the selected analytical procedure again having varied the influence of the at least one desired parameter $P_d$ of interest to the user to produce a second simulation $I_2$ of radiation leaving the sample 30, and compares the first and second simulations $I_1$ and $I_2$ to determine the area or areas where the difference between the first and second simulations is greatest to enable an experiment to be conducted in the area or areas most sensitive to the at least one desired parameter.

Generally, the computer system may produce the first simulation without taking into account the at least one desired parameter $P_d$ of interest to the user. In such a case, the variation in the influence of the at least one desired parameter will be to take that parameter into account. In other cases, the variation in the influence of the at least one desired parameter may be to vary the actual value or range of values of the at least one desired parameter between the first and second simulations.

A method in accordance with the invention allows an inexperienced user to set up an appropriate experiment with the assistance of the computer system which effectively forms an expert system storing available information on possible appropriate analytical procedures to enable the analytical procedure most appropriate to the problem in hand to be selected. Moreover, by comparing the first simulation which may not take into account at least one desired parameter $P_d$ with the second simulation which does take into account the at least one desired parameter, a method in accordance with the invention enables the area or areas most sensitive (that is the area or areas at which the difference between the first and second simulations is greatest) to the at least one desired parameter to be determined so that, within the constraints of the experimental set up, the best possible and most accurate value or values for the at least one desired parameter can be obtained.

The computer system 10 may subsequently control analytical apparatus to cause an experiment to be carried out using the analytical procedure to be conducted in the area or areas most sensitive to the at least one desired parameter. The analytical apparatus may thus be controlled automatically so that an inexperienced user does not need to be advised how to set up the analytical apparatus.

Figure 2:
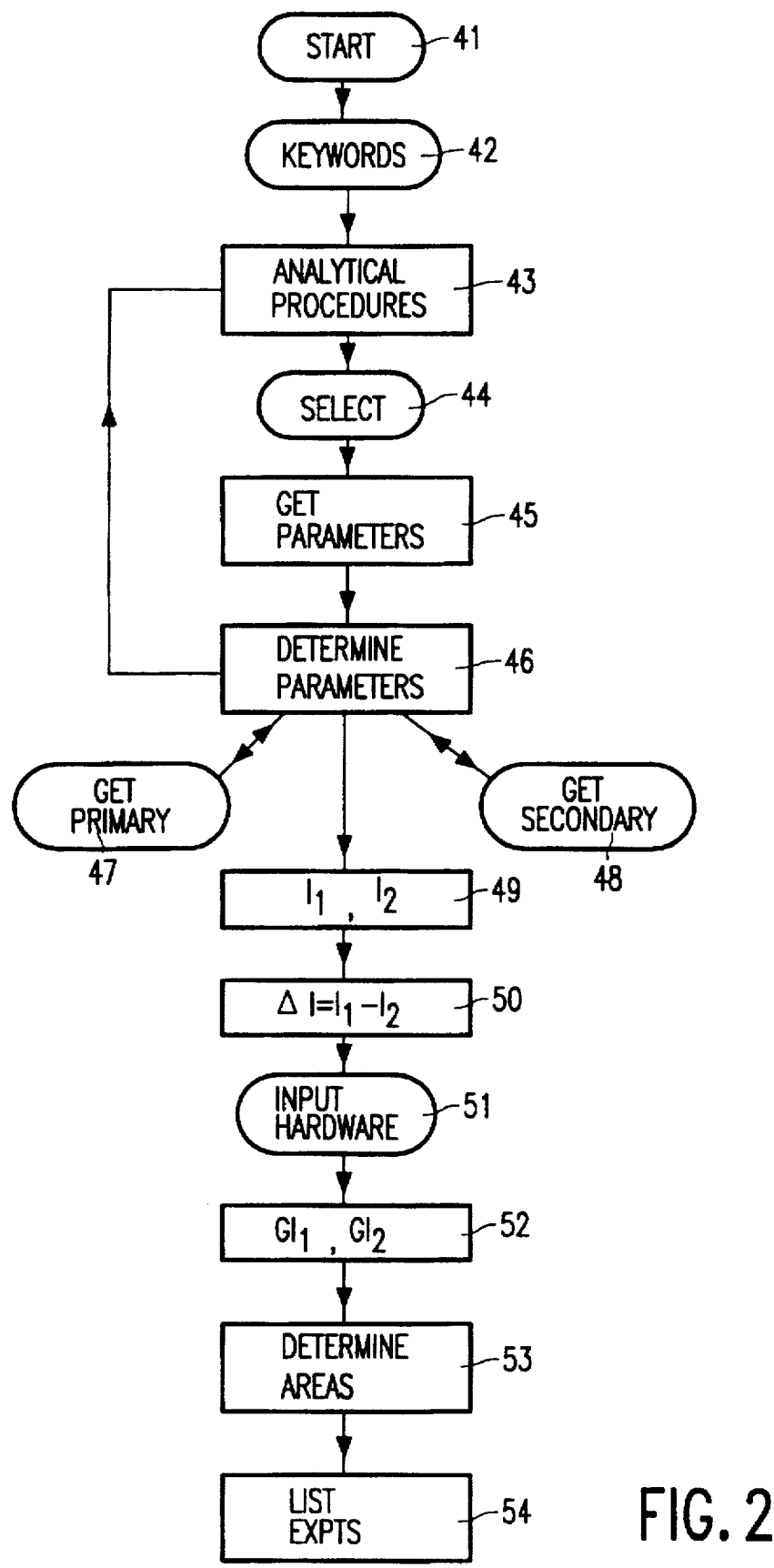
FIG. 2 is a flow chart for illustrating one particular method in accordance with the invention.

Turning now specifically to the drawings, FIG. 2 shows a simplified flow chart for illustrating a particular method in accordance with the invention for designing an experiment such as an X-ray diffraction or scattering experiment, while FIG. 1 illustrates an arrangement 1 suitable for use in such a method including the computer system 10 coupled to one example of an apparatus, in this case an X-ray diffractometer, 20 suitable for use with such a method.

The computer system 10 which may be any suitable conventional digital computer system and could be in the form of a workstation, standalone personal computer or a terminal connected to a mainframe computer. The computer system 10 has a conventional core or "motherboard" 10 consisting of the usual central processing unit, memory, and associated video display drivers etc. and storing the appropriate program of instructions.

The computer system 10 is provided with a first data base DB1 storing digitally information relating to a number of possible X-ray diffraction analytical procedures AP. The information is stored in a known manner using conventional data base techniques to enable access by keywords to be input or selected by a user. The first data base DB1 may, for example, be in the form of a look up table. Generally, the first data base DB1 includes, in addition to the algorithms or names of the algorithms, information on the parameters required to enable simulation of the analytical procedure with the parameters being divided, as will be explained below, into primary and secondary values. If a particular parameter has a relatively fixed value across a wide range of material samples, then the actual value of that parameter or a range for that parameter may be stored in the first data base DB1.

Although the algorithms could, as indicated above, be stored in the first data base DB1, generally the actual algorithms for enabling the analytical procedures to be simulated will be stored in a separate digital storage data base DBA.

The computer system 10 has, in this example, a second data base DB2 which stores digitally available known information likely to be useful in identifying a material sample such as atomic weights for elements, compositions for chemical compounds and common alloys or mixtures and known scattering factors and possibly crystal structure information for common elements or materials. Such information may be added to from time to time and may, for example, include information obtained from previous experiments carried out using the computer system 10.

A third data base DB3 is also provided which stores digitally information on a number of different types of diffractometer apparatus, in particular information (hereinafter known for simplicity as the instrument profile) which enables the effect a particular apparatus has on the diffraction pattern to be simulated. Again, this information may be stored in any suitable fashion which enables it to be accessed via either the name or code given to the apparatus by its manufacturer or by the input by the user of keywords to identify the characteristics of the apparatus.

Where apparatus is specifically manufactured and intended for use in a method in accordance with the invention, then the apparatus may be supplied, for example by means of a floppy disc, with its own instrument profile which can then be added to the data base DB3 by the user. If for some reason there is no information available on the particular apparatus to be used for an experiment, as may be the case if the apparatus is custom-built or has been specially modified, then the user will be requested at the appropriate stage to carry out certain standard experiments to enable the required information for the instrument profile of that apparatus to be obtained and then stored in the data base DB3. Of course, such a process generally need only be carried out once for a particular apparatus because the instrument profile can be stored in the data base DB3 for future use. This latter possibility of course allows for greater flexibility because it enables an instrument profile for an unknown or non-commercial diffractometer to be determined.

The data bases DB1, DB2, DB3 and DBA may be provided in any suitable conventional form, for example on a hard disc of the computer system 10 or on CD-ROM.

The computer system 10 also has a display 2, normally a Cathode Ray Tube (CRT) or Liquid Crystal Display (LCD), although any suitable form of display may be used. An input device 3 is provided for enabling information to be input to the computer system 10 by the user. The input device 3 will generally be a keyboard input device, possibly accompanied by a mouse or like input device, although other forms of input device may be used.

In this particular example, the computer system 10 is also arranged to control operation of an X-ray diffractometer 20 for carrying out a method in accordance with the invention. This enables the experiments which the method in accordance with the invention has determined are most suitable for obtaining the desired parameter $P_d$ to be carried out automatically once the user has signified his acceptance of the proposed method. Of course, however, the diffractometer could be completely separate from the computer system 10 and could be set up independently of the computer system 10 by the user on the basis of instructions supplied to the user by the computer system 10.

As shown schematically in FIG. 1, the diffractometer 20 comprises a suitable X-ray source 21 which, in this example, provides a CuK X-ray line. The X-ray source in this example comprises an electron gun 21a which directs a beam of high energy electrons at, in this case, a copper anode or target 21b to generate a beam X of X-rays. Of course, other suitable forms of X-ray source may be used, for example a synchrotron X-ray source could be used.

It should, of course, be understood that the term "beam" is used only for the sake of convenience and that the X-ray "beam" may be continuous or pulsed as appropriate to the X-ray source and as required by the particular experiment to be carried out.

Preferably, the anode 21b is mounted to a rotatable support 21c (shown very schematically in FIG. 1) so as to enable the anode 21b to be rotated to allow the X-ray beam X to be altered from a point to a line source or vice versa to enable a change in resolution to meet the requirements of the experiment. As indicated schematically in FIG. 1, the rotatable support 21c may be rotated by a motor M1, such as a stepper motor, under the control of the computer system 10.

The X-ray beam emitted from the anode 21b passes through a window 21d of the X-ray source 21 and thence through an entrance aperture or slit 22 which serves to define the X-ray beam X. The size of the entrance aperture or slit 22 may be adjustable by means of a second motor M2 which may also be controlled by the computer system 10.

In the present example, a curved single crystal monochromator 23 is used to enable the unique selection of a single characteristic line. Of course, any suitable form of monochromator may be used, for example the four crystal monochromator disclosed in European Patent Application EP-A-0 1 10 469 and United States Patent U.S. Pat. No. 4,567,605. Again, as indicated schematically in FIG. 1, movement of the monochromator 23 may be by way of a motor M3 controlled by the computer system 10.

Although FIG. 1 shows the use of a monochromator, any suitable form of means for modulating the X-ray beam may be used, for example, one or more slits may be used to modulate the X-ray beam. Such slits may, like the entrance slit 22, be adjustable by means of a motor which may also be controlled by the computer system 10.

A sample support 24 for receiving a sample 30 and a detector system 25 are mounted to a suitable known form of goniometer (not shown) which enables relative ω' and ω rotation of the detector system 25 and the sample support 24 about the centre C of the goniometer. Again, although not shown, this movement may be controlled by the computer system 10. The sample support 24 is also mounted to the goniometer so as to allow two additional angular movements φ and χ about a normal to the sample 30 and about an axis in the plane of the sample, respectively, as illustrated schematically in FIG. 1 to enable the fact that diffraction spots are three-dimensional to be taken into account. Again this movement may be effected by means of one or more motors (one motor M4 being shown) under the control of the computer system 10. Although not shown in FIG. 1, means may also be provided for enabling translational movement of the sample support 24 about three mutually perpendicular axes (conventionally x, y and z) to allow precise positioning of the sample 30 mounted to the support 24.

The detector system 25 may comprise any suitable form of detector 25a such as a proportional counter, a scintillator plus photon counter or a linear or two-dimensional charge-coupled device or thin film photosensitive array associated, where necessary, with an appropriate energy conversion device for converting X-rays into radiation detectable by the array. The use of a position-sensitive, preferably solid state, X-ray detector 25a should improve data collection time.

The X-ray beam passes from the sample 30 through an exit aperture or slit 26 which serves to define the acceptance angle or direction of the X-ray beam X before reaching the detector 25a. The size of the exit aperture or slit 26 may, like the entrance slit 22 be adjustable by means of a motor M5 which may also be controlled by the computer system 10. Of course, depending upon the particular type of detector used, there may be no need for an exit slit 26. The ability to alter the size of the entrance and exit slits 22 and 26 allows the resolution or sample region to be changed if desired or the same resolution or sample region to be maintained over large regions of diffraction space.

If considered desirable, an analyzer 27 may be provided between the sample 30 and the detector 25a. The analyzer 27 may, as shown, be a multiple bounce analyzer crystal as described in, for example, a paper entitled "A High-Resolution Multiple-Crystal Multiple-Reflection Diffractometer" by the present inventor published in the Journal of Applied Crystallography in 1989 in volume 22 at pages 64 to 69.

Although FIG. 1 shows a reflection type of diffractometer, it will of course be appreciated that the present invention could be applied to a transmission type of diffractometer.

The general principles of one particular method in accordance with the invention will now be described with reference to FIGS. 1 and 2 followed by specific examples of the application of such a method to particular problems.

Upon activation of the computer system 10 to carry out a method in accordance with the invention as indicated at block 41 in the simplified flow chart shown in FIG. 2, an introduction or welcome screen is displayed to the user on the display 2 explaining the purpose of the method.

The user is then requested (step 42 in FIG. 2) by a new image on the display 2 to input details of the material sample which he wishes to analyze and the nature of the desired parameter or parameters of the sample which he wishes to determine. The computer system is preferably set up to guide the user so that when the user enters the first letter or letters of a possible keyword, the computer system 10 will show on the display 2 a list of all the actual keywords beginning with that letter or letters.

Although in this example the user simply inputs the information available and the computer system 10 extracts the relevant data, the data input could be by way of a menu driven system in which the user selects, using the keyboard 3 or other suitable input device such as a mouse or light pen, one or more initial keywords shown on the display 2 and then is prompted for further information until sufficient information has been obtained to enable the computer system to use the keywords selected by or determined from the information input by the user to select using the data base DB1 the analytical procedure or procedures that may be suitable for obtaining the information required by the user.

The information regarding the analytical procedures AP in the data base DB1 is stored so that the address of the information on a given analytical procedure is related to particular keyword or keywords. Accordingly, once the user has input or selected the appropriate keyword or keywords, the computer system 10 retrieves from the data base DB1 the information for the or each analytical procedure AP associated with the selected keyword or keywords by effectively using the entered or selected keywords. In the particular method of FIG. 2, the computer system then displays information regarding the or each analytical procedure AP associated with the selected keyword or keywords to the user on the display 2, as indicated at step 43 in FIG. 2.

The display 2 may show, for each possible analytical procedure AP, a brief description explaining the analytical procedure and may also identify the information or basic parameters required to be known to enable the desired parameter $P_d$ to be determined to assist the user in the choice of the analytical procedure or method. At this stage in this particular method, as indicated by step 44 in FIG. 2, the user is requested to select one of the displayed analytical procedures. This may be done by requesting the user to input using the input device 3, a code associated on the display with the analytical procedure he wishes to select or by requesting the user to select the desired analytical procedure by selecting or clicking on an appropriate part of the display 2 using a mouse or other similar input device.

Once the user has made his selection, the computer system 10 interrogates at step 46 the data base DB1 or the selected analytical procedure in the data base DBA to determine the list of parameters required to enable the selected analytical procedure AP to be simulated.

The required parameters for each analytical procedure will normally include primary parameters whose values must be known to enable the simulation to be carried out and secondary parameters which can have default, or estimated values or can be refined (that is parameters having only a minor (or second order) effect on the diffraction pattern simulated by the algorithm for the selected analytical procedure or parameters, including the desired parameter $P_d$ which can be refined or adjusted).

Once the computer system 10 has determined from data base DB1 or DBA what primary and secondary parameters are required to enable the selected analytical procedure to be simulated, the user will be advised via the display 2 of the primary and secondary parameters required to simulate the selected analytical procedure. The computer system 10 then requests at steps 47 and 48 the user to supply values for the primary and secondary parameters required to simulate the selected analytical procedure. If the user is unable to supply the necessary values for a primary parameter and the computer system 10 cannot locate a value for such parameter in the data base DB2 (if available), then the computer system 10 may search using the data base DB1 for another analytical procedure which does not require that missing parameter and will repeat steps 43 to 48. Alternatively, or if another such analytical procedure is not available, the computer system 10 will search for analytical procedures for determining the missing primary parameter and will advise the user that a preliminary experiment needs to be carried out to determine the missing primary parameter. Of course, where the diffraction apparatus 20 is coupled to the computer system, then certain parameters, such as the operating wavelength may be obtained, for example down-loaded, from a memory store of the apparatus, directly from the apparatus.

If information on a secondary parameter is not available either from the user or the data base DB2, then the computer system 10 may use a default or expected value associated with the algorithm for simulating that particular analytical procedure AP or may request the user to input a guess or likely range for the missing secondary parameter. Where, for example, the primary interest is in the crystallite size in the sample, typical primary parameters required are the X-ray wavelength to be used for the experiment and the chemical composition of the material from which the sample under investigation is made while a typical secondary parameter may be an estimate of the crystallite size, determined from information regarding, for example, the growth conditions of the sample.

Once the necessary primary and secondary parameters have been obtained, the algorithm stored in data base DBA for the selected analytical procedure AP is used to simulate the diffraction pattern for an ideal diffractometer, that is a diffractometer for which the instrument profile is constant over the entire diffraction space of interest. As indicated by step 49 in FIG. 2, a first diffraction pattern $I_1$ which does not take into account the parameter of interest is first calculated and then a second diffraction pattern $I_2$ which does take into account the parameter $P$, of interest is calculated.

The first and second diffraction patterns $I_1$ and $I_2$ are then normalised and compared at step 50 by subtracting for each predetermined point (that is a predetermined 2θ value) in diffraction space the value of one of the first and second diffraction patterns $I_1$ and $I_2$ from the other so as to determine for each point in diffraction space the difference between the two patterns. The computer system 10 then determines where in diffraction space this difference is greatest to select the region or regions of diffraction space, for an ideal diffractometer, most sensitive to the parameter of interest so as to decide the region or regions of diffraction space within which the actual experiment should be carried out.

A list of possible experiments is generated and ordered in terms of sensitivity to the parameter of interest. This list may be shown to the user on the display 2 so that the user is kept involved in the process.

At this stage in the particular method of FIG. 2, the simulation has been carried out for an ideal diffractometer. The appropriate instrument profile for the apparatus to be used is then determined by requesting the user at step 51 to input information concerning the hardware, that is the diffractometer, to be used or by, for example, requesting the user to select the diffractometer from a list displayed on the display 2. Of course, where more than one diffractometer is available, then the computer system 10 will consider all the available diffractometers and advise the user (or choose if the computer system controls the diffractometer automatically) the most appropriate diffractometer for the experiment. The information or instrument profile IP convolutes for the selected diffractometer are then obtained from the data base DB3 or down-loaded from the apparatus itself. The instrument profiles may be stored in data base DB3 in part in algorithmic form and in part in the form of actual numeric values for settings etc. Effectively, for each diffractometer, the stored instrument profile provides a convolute for each possible setting of the diffractometer for all the accessible regions in the diffraction pattern.

Once the requisite instrument profile IP has been determined, then, for each possible diffractometer setting, the normalised first and second diffraction patterns $I_1$ and $I_2$ are separately convoluted with the instrument profile at step 52 and the difference between the two convolutions $GI_1$, and $GI_2$ is determined, for each possible diffractometer setting, in a manner similar to that described above to determine the effect of the instrument profile IP on area or areas of diffraction space most sensitive to the desired parameter $P_d$. The list of experiments is then reordered in accordance with the effect of the instrument profile. The order of the experiments will now depend upon the parameter of interest, the diffraction effect and the settings and type of diffractometer to be used.

It may be possible, at least in some circumstances, to convolute the already-obtained difference profile (that is the difference between corresponding points in diffraction space between the first and second diffraction patterns) with the instrument profile convolutes rather than have to convolute the first and second diffraction patterns $I_1$ and $I_2$ separately with the instrument profile convolutes and then redetermine the difference.

Where computing power is not a problem, then the step of comparing the normalised first and second diffraction patterns before convolution with the instrument profile convolutes may be omitted. The inclusion of such a step does however have the advantage of enabling any areas of diffraction space in which the desired parameter $P_d$ has no significant effect to be omitted from the convolution with the instrument profile convolutes which should reduce computation time.

The possible list of experiments may then be ordered at step 53 in terms of accuracy and/or time required for the experiment and a list of experimental choices with their associated accuracy, (sensitivity to the desired parameter), the diffractometer to use, diffractometer settings, time required for experiment and so on, displayed to the user at step 54 on the display 2.

The user then makes his selection and, in the case of apparatus such as that shown in FIG. 1, the computer system 10 controls the diffractometer 20 to set up and carry out the desired experiment or experiments by supplying control signals to the appropriate motors and other control components within the diffractometer 20. Of course, where more than one diffractometer is available, the computer system 10 may be linked to each diffractometer.

Figure 3:
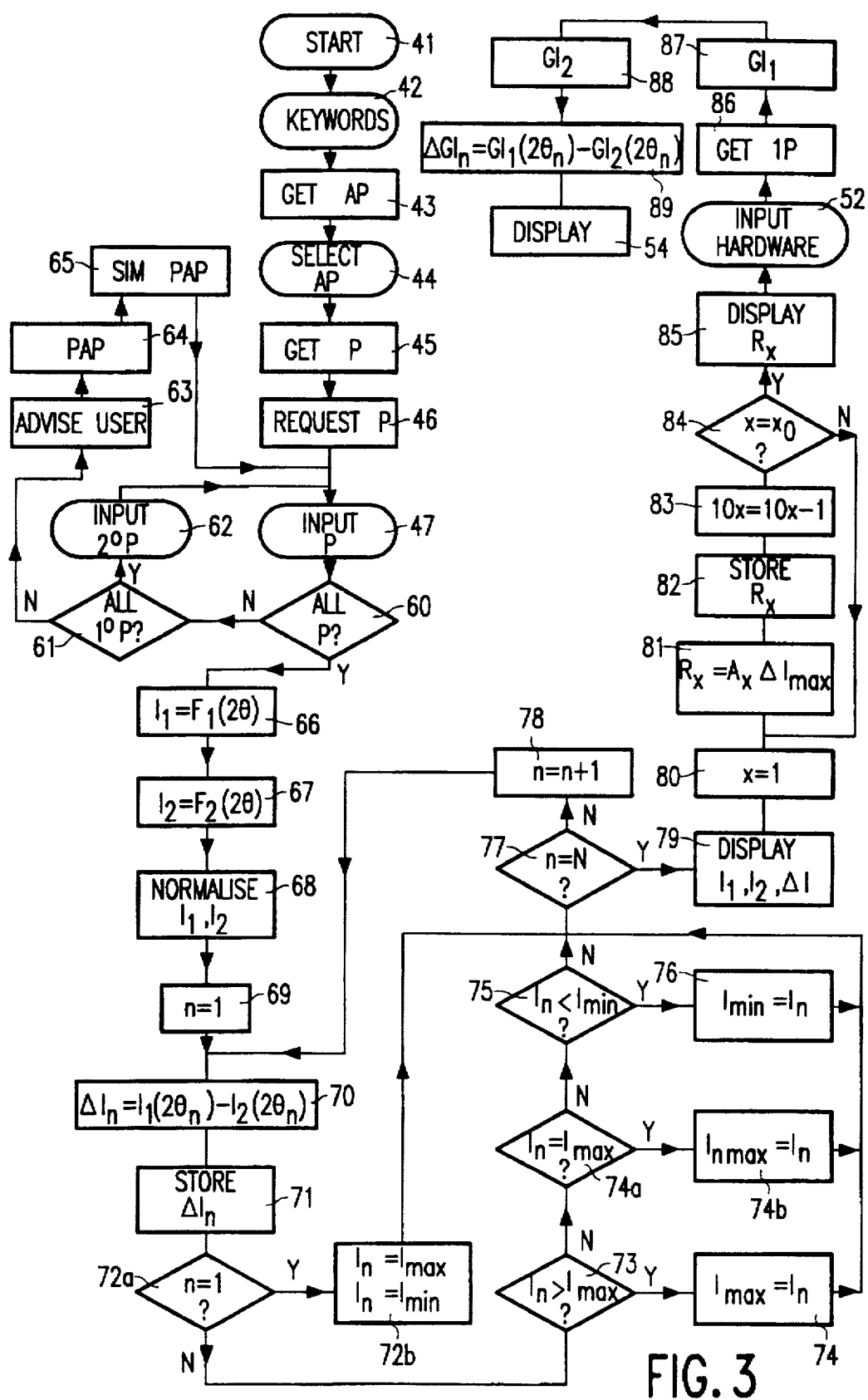
FIG. 3 is a flow chart for illustrating in more detail one example of such a method in accordance with the invention.

FIG. 3 illustrates one possible example of a particular method in accordance with the invention, with the steps from the determination of the required parameters being shown in greater detail than in FIG. 2.

Thus, the particular method illustrated in FIG. 3 proceeds as indicated in FIG. 2, up to the request at step 46 for the required parameters to be input. Once the user has input at step 47 all the information he has available on the required parameters, the computer checks at step 60 whether values have been obtained for all the required parameters P. If the answer is yes, the computer system 10 proceeds to the simulation as will be described below. If, however, the answer is no, then the computer checks at step 61 whether values have been obtained for all the primary parameters P1. If the answer is yes, then the computer system requests at step 62 the user to either input a guess or supply a range, or to request the computer system 10 to obtain a default value or range from the appropriate data base DB2, for the unknown secondary parameter or parameters.

If the computer system 10 determines at step 61 that the unknown parameter is a primary parameter P1, then the user will be advised at step 63 that a preliminary simulation will have to be carried out to determine a value for the missing primary parameter and the computer system 10 then selects at step 64 a preliminary analytical procedure PAP from the data base DBA using the name of the unknown parameter as a keyword to find the primary analytical procedure in the data base DB1. The necessary preliminary analytical procedure or procedures are then carried out at step 65 to determine a value for the missing primary parameter P1. Although not shown in detail in FIG. 3, the procedure for simulating the unknown primary parameter may be the same as or similar to that to be finally used for determining the experiments to be carried out to obtain the desired parameter $P_d$ and so may result, effectively, in instructions to the user to carry out initial experiments to determine the unknown primary parameter P1. Alternatively, depending upon the nature of the particular unknown primary parameter P1, the preliminary procedure may simply consist of the use of an appropriate algorithm to determine a value for the unknown parameter.

As indicated in FIG. 3, steps 61 to 65 are repeated until the computer system 10 has a value for all the parameters required to carry out the simulations to determine the effect of the parameter $P_d$ desired to be known by the user. Once all the required parameters are known, the computer system 10 uses the stored algorithm for the selected analytical procedure AP at step 66 to produce the first simulation or first diffraction pattern $I_1$, as a function $f_1$ of 2θ ($I_1=f_1(2θ)$) where $f_1$ does not take into account the desire parameter $P_d$ and carries out at step 67 the second simulation to produce a second diffraction pattern $I_2$ as a function $f_2$ of $2\theta$ ($I_2=f_2(2\theta)$) taking into account the desired parameter $P_d$.

The first and second simulations $I_1$ and $I_2$ are then normalised at step 68 using any suitable normalisation process which, for each simulation, makes the maximum value of I equal to 1 or some other fixed number. Of course, the normalisation procedure for the first simulation $I_1$ could be carried out before the second simulation.

Next, the computer system 10 proceeds to determine the difference between $I_1$ and $I_2$ for each selected value of $2\theta$ where $2\theta$ increases in, predetermined steps of $\Delta\theta$ and thence to select the areas of diffraction space where the difference is greatest. FIG. 3 illustrates one possible way of achieving this. As shown in FIG. 3, the computer system 10 first sets a counter to n=I at step 69 and then at step 70 determines the difference:

$$\Delta I_n = I_1(2\theta) - I_2(2\theta_n)$$

for that value of $2\theta$.

The computer system 10 then stores $\Delta I_n$ step 71. If n=I, the computer stores the initial value of $\Delta I_n$ as $\Delta I_{max}$ and $\Delta I_{min}$ as indicated by steps 72a and 72b in FIG. 3. If n is not equal to 1, then the computer system 10 checks at step 73 whether $\Delta I_n > \Delta I_{max}$ and if so stores (step 74) the value of $\Delta I_n$ as the maximum value $\Delta I_{max}$. If the answer is no, the computer system 10 checks at step 74a whether $\Delta I_n = \Delta I_{nmax}$ and if so stores it at step 74b as $\Delta I_{nmax}$ so that all maximum values $\Delta I_{nmax}$ and their related $2\theta$ values are stored. If it is determined at step 75 that $\Delta I_n < \Delta I_{min}$ the new value of $\Delta I_n$ is stored at step 76 as the new minimum value $\Delta I_{min}$. Then, as indicated at step 77, the computer system 10 checks whether n=N, where N is the number of values of $2\theta$ for which the comparison is being made. If the answer is no, the computer increments the counter at step 78 and repeats steps 70 to 77 until n=N at which time a difference value $\Delta I_n$ will have been stored for each $2\theta_n$ and the actual minimum and maximum values $\Delta I_{min}$ and $\Delta I_{max}$ will have been stored, together with any other maximum values $\Delta I_{nmax}$.

When the answer to the question at step 77 is yes, the computer system 10 may on display 2, as indicated by step 79 in FIG. 3, the first and second diffraction patterns $I_1$ and $I_2$ and the difference values $\Delta I_n$. Preferably, these values are displayed graphically as $I_1$, $I_2$ and $\Delta I_n$ against $2\theta$, although a list of numerical values could be displayed.

The computer system 10 then goes onto determine the area or areas of diffraction space most sensitive to the desired parameter $P_d$, that is those in which the difference $\Delta I$ is greatest using any suitable approach. In this example, the computer system 10 first of all sets a counter x=I at step 80 and then selects at step 81 areas $R_x=Ax\ \Delta I_{max}$ of diffraction space (that is ranges of $2\theta$) surrounding each $\Delta I_n$ which is equal to $x\Delta I_{max}$. Each area A has either a fixed width or range in $2\theta$ about the x $\Delta I_{max}$ or a width about the x $\Delta I_{max}$ limited by the $2\theta$ values at which x $\Delta I_n$ drops to a given percentage, say 90% for example, of $x\Delta I_{max}$. The actual percentage of x $\Delta I_{max}$ may be determined to be a given fraction of the difference between the $\Delta I_{min}$ and x $\Delta I_{max}$ values. These areas $R_x$ are then stored as indicated at step 82.

As illustrated in FIG. 3, this procedure may be repeated to define successively less sensitive areas by decrementing x (in this example setting 10x=10x-1 at step 83) and then repeating steps 81 to 83 until the computer system determines at step 84 that $x=x_o$, where $x_o$ is a predetermined value. The areas $R_x$ of diffraction space are thus stored for each value of x and may then be displayed to the user at step 85 to indicate the areas of diffraction space which should be explored and also to show the sensitivity of the area $R_x$ to the desired parameter, with, of course, the sensitivity decreasing with x.

The user is then requested at step 51 (see FIG. 2) to input information regarding the hardware, that is the diffractometer or diffractometers that are available for an experiment. This input may be achieved in a similar manner to the input of information at step 42, that is by the user inputting or selecting keywords. The computer system 10 uses these keywords as addresses to select at step 86 the appropriate instrument profile IP. Of course, although not shown in FIG. 3, if the computer system 10 cannot find an instrument profile associated with the information input by the user or the user does not have the necessary information, then the computer system 10 will instruct the user to carry out one or more standard experiments from which the necessary information regarding the apparatus to be used can be derived. Where the computer system 10 is linked to the diffractometer, then information, such as the operating wavelength, may be fed back to the computer system 10 by the diffractometer.

Once the instrument profile IP has been determined, then the computer system convolutes the normalised diffraction patterns $I_1$ and $I_2$ with the instrument profile IP at steps 87 and 88 to obtain the convolutes $GI_1$ and $GI_2$. The areas of greatest sensitivity are then determined by finding $\Delta GI_n$ for each value of, for example, $2\theta$ as indicated at step 89. This may be achieved by basically carrying out steps similar to steps 69 to 84 on the convolutes $GI_1$ and $GI_2$ rather than on the first and second diffraction profiles $I_1$ and $I_2$ and accordingly the steps involved will not be discussed in detail. This procedure may be carried out for the entire range of $2\theta$ or simply for the areas $R_x$ previously identified. Of course, similar steps may be carried out for other angular variables such as $\omega$, $\chi$ or $\phi$ in addition to $2\theta$ to determine the areas of interest.

A list of possible experiments and their accuracy is then displayed to the user at step 54. This list will show the experiments, that is the instrument settings and the areas of diffraction space in which the experiments are to be carried out, for each $R_x$ with the experiments listed in order of their sensitivity to the desired parameter. Where the information is obtainable from the instrument profile IP or information input about the diffractometer 20, the list may also include appropriate times for the experiments. As indicated above, the computer system 10 may be used directly to control the diffractometer or selected one of the diffractometers.

To give one example of a specific analytical procedure, suppose the user is interested, as mentioned above, in determining the most appropriate experiment to obtain the average crystallite size in a polycrystalline material sample. In such a case, when the user inputs or selects (as described above at step 42 in FIG. 2) text which includes one or more of the following keywords:

size
broadening
particle
crystallite
grain
length
scale

The computer system 10 then selects at step 43 in FIG. 2 or 3 the possible analytical procedures for determining the effect of size. Then, in the particular method of FIGS. 2 and 3, the display displays at step 44, a brief description of the algorithm. In the present case, there may be three or more possible analytical procedures but for the sake of simplicity only one (the one actually selected by the user) will be described here.

The display 2 may show the following message for the algorithm for this particular analytical procedure:

> This algorithm will model the influence of the average crystallite size in a bulk material on the diffraction profile Assuming the user selects this analytical procedure at step 44, the computer system 10 will then request the user to supply at least some of the information to obtain the required parameters. In the present case the required parameters can be divided into three types, identified as follows:

STRUCT: bulk structural information about the sample
MICRO: structural information about the microscopic nature of the material, for example the characteristics of a grain
TUBE: information about the X-ray source In the present example, the parameters required are:
Primary parameters:

---
STRUCT
θ
MICRO
strain
TUBE
λ

---

Secondary parameters:

---
STRUCT
none required
MICRO
size
TUBE
Δ   λ

--- where θ are the Bragg angles for the peaks to be measured and are determined from λ and the material of the sample 30 using data base DB2, "strain" is the distribution of strain in a grain, that is the microstrain, λ is the wavelength supplied by the X-ray source, Δλ is the wavelength band pass of the experiment about λ and "size" is a guess at the value of the parameter $P_d$ desired to be determined. It will of course be appreciated that λ could also be a variable choice, that is it could be a secondary parameter, if the diffractometer or choice of diffractometers allows for variations in λ.

Assuming that the user is able to supply (or the computer system 10 can provide default values or ranges) at step 47 these parameters or information that will enable them to be determined, the computer system 10 then calculates the diffraction pattern $I_1$ step 66 in FIG. 3) without taking into account the crystallite size using Bragg's law (nλ=2d sin θ). The diffraction pattern $I_2$ taking into account the crystallite size is calculated (step 67 in FIG. 3) using the information stored in the data base DB1 or the algorithm data base DBA that the crystallite size produces broadening of the diffraction peaks in a well-defined manner in accordance with the Scherrer equation:

$$\beta = \frac{K\lambda}{\text{size}\cos\theta}$$

where β is the width of the peak, θ is the Bragg angle, λ the wavelength and K is a constant. Thus, effectively, each peak of the first diffraction pattern DB1 is broadened or convoluted with a Lorentzian (Cauchy) profile of width β derived from its θ position and the estimated crystallite size to produce the second diffraction pattern $I_2$.

The first and second diffraction patterns $I_1$ and $I_2$ are then normalised (step 68 in FIG. 3) and their values for each of given selected points (obviously the closer together the points selected the greater the accuracy of the comparison) in diffraction space subtracted from one another (step 50 in FIG. 2, at steps 69 to 85 in the example of FIG. 3) to determine the area or areas $R_x$ of the diffraction space most sensitive to the crystallite size, that is the area or areas for which the difference $\Delta I_n$ between the first and second diffraction patterns $I_1$ and $I_2$ is greatest.

After the user has input (step 51 in FIGS. 2 and 3) the information about the diffractometer to be used to enable the appropriate instrument profile [P to be selected from data base DB3 (step 86 in the example of FIG. 3), the effect of the actual diffractometer to be used is determined by, for each possible diffractometer setting, convoluting the results of the first and second diffraction patterns $I_1$ and $I_2$ with the instrument profile IP as described above at step 51 in FIG. 2 and as illustrated in detail by steps 87 to 89 of the example shown in FIG. 3.. The possible experiments are then displayed to the user on the display 2 (step 54 in FIGS. 2 and 3) indicating their sensitivity to the desired parameter and, where this can be determined by the simulation, the accuracy of and time required for the experiment. Once the user has selected one of the possible experiments, then the computer system 10 may instruct the user to mount the sample to be investigated to the sample holder 24 and may automatically set up the or the chosen diffractometer 20 to carry out the experiment once the sample 30 has been correctly positioned by the user.

Figure 4:
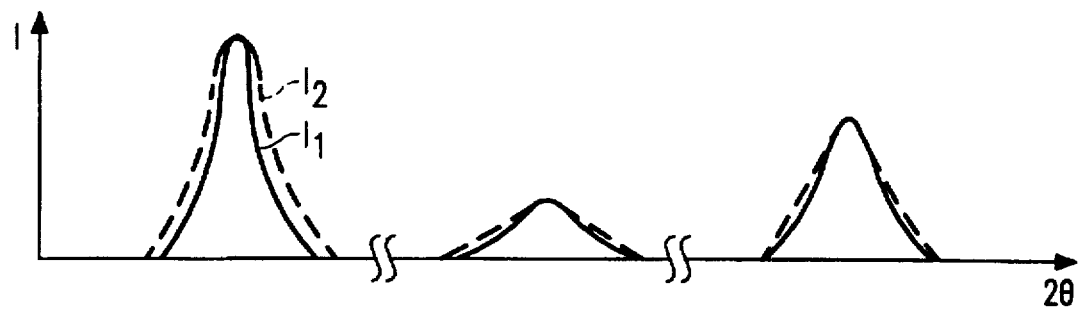
FIG. 4 illustrates graphically the results of first and second simulations of a given analytical procedure.
Figure 5:
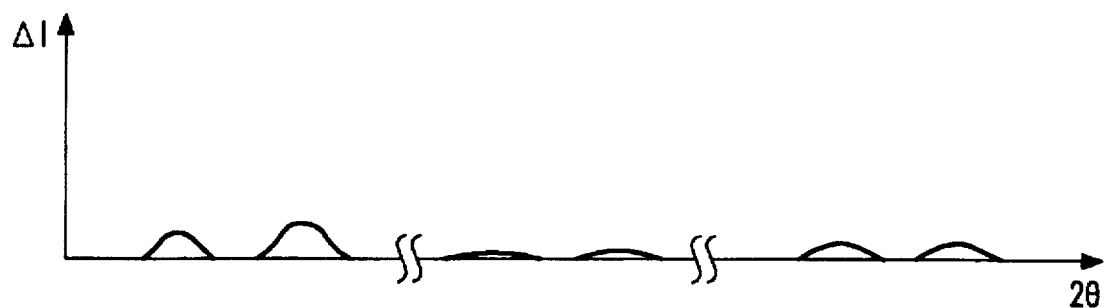
FIG. 5 illustrates graphically the results of the comparison of the first and second simulations shown in FIG. 3.

FIGS. 4 and 5 illustrate typical graphs which may be displayed to the user on the display 2. FIG. 4 shows a graph of intensity I against 2θ with the solid curve showing the first simulation $I_1$ for the 'ideal' diffraction profile and the dashed curve showing the second simulation $I_2$ which incorporates the effect of size on the ideal profile. FIG. 5 plots the difference ΔI between the first and second simulations $I_1$ and $I_2$ and so shows the user where this difference is greatest, that is the areas most sensitive to the influence of crystallite use.

The information shown on the graphs of FIGS. 4 and 5 could be directly used to set up the diffractometer 10 although it may be preferable, especially for an inexperienced user, for written suggestions for experiments and instructions for setting up the diffractometer to be supplied to the user by the computer system 10.

To take another example, suppose the user wishes to determine the appropriate experiment or experiments to discover the amount of phase A in a material sample in which phases A and B have partially reacted to produce phase C.

Thus, the reaction type is:

(1) A+B>>>C+? for a complete reaction.
(2) A+B>>>A+B+C+? for a partially reaction.

and the information ultimately wanted is simply the proportion of A by weight in (2). As in the example given above, the user inputs or selects keywords (step 42 in FIGS. 2 and 3) which in this case might be any one or more of:
proportion
weight
phase
ratio
component The computer system 10 then searches the keywords associated in data base DB1 with each analytical procedure until it finds one or more analytical procedures associated with the keyword(s) input or selected by the user (step 43 in FIGS. 2 and 3). Again, although the computer system 10 may find two or more analytical procedures associated with the input or selected keywords, in the interests of simplicity, only the analytical procedure actually selected by the user will be discussed.

The computer system 10 then displays (step 44 in FIGS. 2 and 3) to the user a description of each located analytical procedure, for example for the analytical procedure the user ultimately selects in this example, namely METHOD: PORTION_W:, the description may be:

This method determines the weight fraction of a phase in a partially reacted material, where not all of the phase components are known and one of them is available in its pure form.

It should be understood that as used herein, the work 'phase' may mean a different actual phase of the same material or a different element or compound.

The computer system 10 may also display further information about the analytical procedure to assist the user in understanding the procedure, for example:

EXPLANATION OF METHOD: PORTION_W:

The proportion by weight of the phase A in the sample is given by:

weight proportion of $A = w_o(A)/(w_o(A)+w_o(B)+w_o(C)+w_o(?))$

If a series of samples (i) is created by adding a known weight $W_i(A)$ of phase A in its pure form then the weight proportion of A is given by:

$\{W_i(A)+w_o(A)\}/\{w_o(B)+w_o(C)+w_o(?)+W_i(A)\}$ and the proportion by weight of the phase C in the sample is:

$\{w_o(C)\}/\{w_o(B)+w_o(C)+w_o(?)+W_i(A)\}$ dividing these two equations to obtain the intensity ratio for selected diffraction lines of A and C, gives an intensity ratio.

$\{W_i(A)+w_o(A)\}/\{w_o(C)\}=\{I(A)/I(C)\}_i K$ where i is the number of the experiment. A graph of the intensity ratio versus the weight ratio has an intercept w(A) and a slope w(C).

In order for an appropriate experiment to be selected, the accuracies in the derivation of w(A) and w(C) must be considered. In this case, the algorithm for the selected analytical procedure assumes that the weighing accuracy greatly exceeds the reliability of the intensity measurement and that the following variance should be considered: $\sigma^2(\{I(A)/I(C)\}_i K)$, hence:

$$\sigma^2\left(\frac{I(A)}{I(C)} K\right) = \left(\frac{K}{I(C)}\right)^2 \sigma^2(I(A)) + \left(\frac{I(A)K}{I(C)^2}\right)^2 \sigma^2(I(C)) + \left(\frac{I(A)}{I(C)}\right)^2 \sigma^2(K)$$

For this analytical procedure, the computer system 10 determines that the associated primary parameters, that is the parameters which must have a value for the analytical procedure to be simulated, are:

$W_1(A), W_2(A), \ldots W_n(A)$
$K$
$I_i(A), 2\theta_i(A)$
$I_j(C), 2\theta_j(C)$ where $W_x(A)$ is the weight of element or compound A in the xth sample, K is a parameter which relates the intensity ratio I of a diffraction peak to the weight ratio, $I_i(A)$ and $I_j(C)$ are the intensity ratios of the diffraction peaks for the elements or compounds A and C and $\theta_i(A)$ and $\theta_j(C)$ are the Bragg angles for the element or compounds A and C, respectively. At this stage (step 46 in FIGS. 2 and 3), the computer system 10 also displays to the user the secondary parameters required for the selected analytical procedure, that is those parameters which have only a minor influence or which, like the weight ratio, can be varied or adjusted.

$\sigma(K)$
$2\theta(A)_{min}, 2\theta(A)_{max}$
$2\theta(C)_{min}, 2\theta(C)_{max}$
$I_i(B), 2\theta_i(B)$
$I_j(?), 2\theta_j(?)$
$\Delta 2\theta_i(A)$
$\Delta 2\theta_j(C)$
$\Delta 2\theta_i(B)$
$\Delta 2\theta_j(?)$
$N_{number\ of\ samples}, n$ where $\sigma(K)$ which represents the accuracy of K will simply give a better evaluation of the accuracy in determining w(A) and $2\theta()_{min}$ and $2\theta()_{max}$ are useful in determining the $2\theta$ range for undertaking the comparison of the first and second diffraction patterns $I_1$ and $I_2$. The intensities and scattering angles $I_i(B), 2\theta_i(B), I_j(?)$ and $2\theta_j(?)$ for the other phases would help in the choice of possible reflections for A and C by eliminating overlapped reflections. The $\Delta 2\theta()$ values are the peak widths (which determine the overlap extent) and may have default values. The number N of samples that could possibly be made may help insofar as having a limited number of material samples would have a significant bearing on the accuracy of the result of the experiment.

The parameters which are wanted or desired to be known by the user are, of course:
$W_o(A)$
$\sigma(w_o(A))$
$w_o(C)$
$\sigma(w_o(C))$ namely the actual weight ratios $w_o(A)$ and $w_o(C)$ and associated errors $\sigma(w_o(A))$ and $\sigma(w_o(C))$ for phases A and C.

The computer system 10 displays to the user the primary, secondary and wanted parameters on the display 2 and, as indicated above, requests the user (step 46 in FIGS. 2 and 3) to input any known values for any of the parameters.

The primary parameters must have a value otherwise the percentage by weight w(A) of element or compound A cannot be determined. The values for $W_n(A)$ and the actual value of n, that is the required number of experiments may be input directly by the user or may be variables used by the computer system 10 to provide the user with a list of possible experiments. Different weight ratios can of course be tried once the user has determined how many experiments he is willing to prepare. Alternatively, this also can be indicated by calculation. The latter is determined by comparing the improvement in the precision with N. I() and 2θ() are determined from the data base DB2 which contains information on phase A or C. K is, however, unknown and, moreover, cannot be guessed by the user. The computer system 10 will therefore advise the user (at step 63 in the example of FIG. 3) that the selected analytical procedure cannot be carried out until K has been determined.

The computer system 10 thus now searches the database DB1 to find any analytical procedures associated with the keyword K (step 64 in the example of FIG. 3). In the present example, the computer system 10 identifies two possibilities: OBTAIN_K1 and OBTAIN_K2 and displays the following descriptions to the user on the display 2:

OBTAIN_K1: This module determines the parameter K that relates the intensity ratio to the weight ratio by use of a standard material and the material of interest that exists in another phase mixture. This is a single experiment method that may have limited accuracy.

OBTAIN_K2: This method obtains the value of K that relates the intensity ratio to the weight ratio for an ideal (randomly orientated or texture corrected) polycrystalline data set. It requires a series of standard samples mixed with the sample of interest to obtain a good value of K and an estimate of its error.

If OBTAIN_K1: is selected by the user, the computer system 10 may display on display 2 a brief explanation of the analytical procedure, as follows:

EXPLANATION OF PROCEDURE OBTAIN_K1

K is obtained from the following equation:

$$K = (Wstd/W(A))(I(A)/I(std))$$

where the weights are a proportion of the whole. This cannot be directly applied to our example because there is a component of A in the denominator of the weight ratio and the proportion of the B, C and ? phases are unknown and ? is an unknown phase. But the proportional relationship between intensity ratio and weight ratio can be determined by making a sample with a known $(W_i(A)/W_i(std))$ ratio, where $W_i(A) + W_i(std) = 1$.

For this weight ratio we can then measure an intensity ratio.

$$K = (W_i std/W_i(A))(I_i(A)/I_i(std))$$

The computer system may also display to the user the required parameters, as follows:

| | |
|---|---|
| $I_i(A)$, $2\theta_i(A)$ | PRIMARY |
| $I_i(std)$, $2\theta_i(std)$ | PRIMARY |
| $2\theta(A)\_min$, $2\theta(A)\_max$ | SECONDARY |
| $2\theta(std)\_min$, $2\theta(std)\_max$ | SECONDARY |
| $\Delta 2\theta_i(A)$ | SECONDARY |
| $\Delta 2\theta_i(std)$ | SECONDARY |
| K | WANTED |
| $\sigma(K)$ | WANTED | where $\sigma$, represents the error in a value.

Clearly the accuracy required for K, which will have consequences on the required accuracy for the weight ratio measurement and the intensity ratio measurement, will need to be known. The algorithm for K relates the various errors by:

$$\sigma^2 K = \left(\frac{\partial K}{\partial \left(\frac{W(std)}{W(A)}\right)}\right)^2 \sigma^2\left(\frac{W(std)}{W(A)}\right) + \left(\frac{\partial K}{\partial \frac{I(A)}{I(std)}}\right)^2 \sigma^2\left(\frac{I(A)}{I(std)}\right)$$

and then assumes that the error in the weighing is minimal, leaving the errors in the x-ray intensity measurement:

$$\sigma^2 K = \left(\frac{W(std)}{W(A)}\right)^2 \sigma^2\left(\frac{I(A)}{I(std)}\right)$$

The algorithm for OBTAIN_K1 uses information in the data base DB2 concerning the phases A and STD to calculate the total diffraction pattern for various weight ratios and to find the best pairs of intensities from the two phases that yield the minimum error in K. The intensities as a function of weight are determined by use of a subroutine WEIGHT-INTENSITY which calculates the relationship:

$$I(phase) \propto \frac{(F_{hkl}(phase))^2 \frac{W(phase)}{\rho(phase)}}{\sum_{J=1}^{J=n}\left(\frac{W(J)}{\rho(J)}\right)\bar{\mu}}$$

where $\mu$ is the average linear absorption coefficient for the mixture and $\rho$ is the density of phase. The linear absorption coefficient is given by:

$$\bar{\mu} = \bar{\rho}\sum_{J=1}^{J=N}\left(W(J)\left(\frac{\mu}{\rho}\right)_J\right)$$

Of course, the number of experiments that could be carried out to determine K may in principle be limitless but bounds are set defined by the diffractometer scan limits, the resolution of the instrument and other constraints. The diffractometer resolution $\Delta 2\theta_i(A)$, $\Delta 2\theta_j(std)$ influences the choice because of course the selection of values with overlapping peaks is not desirable. Any such overlap regions may be determined using any suitable approach.

If, alternatively, the preliminary analytical procedure OBTAIN_K2 is selected, then, again, the computer system 10 may display on display 2 a brief explanation, as follows:

BRIEF EXPLANATION OF OBTAIN_K2

The expression $$K = (Wstd)MW(A))(I(A)/I(std))$$

may be evaluated by relating a series of weight ratios for samples of the type:

$$W_1(A)/W_1(std) =_w k_1$$

$$W_2(A)/W_2(std) =_w k_2$$

...

$$W_n(A)/W_n(std) =_w k_n$$

A series of diffractometer scans for each of these samples will then produce peak intensity ratios $I_1(std)/I_1(A)$, $I_2(std)/I_2(A)$, ... $I_n(std)/I_n(A)$. A choice has to made here: the number of samples $N_n$ that you are prepared to make or can make.

Again, the computer system 10 may display to the user a list of the required parameters:

| | |
|---|---|
| $I_i(A)$, $2\theta_i(A)$ | PRIMARY |
| $I_i(std)$, $2\theta_i(std)$ | PRIMARY |
| $2\theta(A)\_min$, $2\theta(A)\_max$ | SECONDARY |
| $2\theta(std)\_min$, $2\theta(std)\_max$ | SECONDARY |
| $\Delta 2\theta_i(A)$ | SECONDARY |
| $\Delta 2\theta_i(std)$ | SECONDARY |
| $N_{number\ of\ samples,\ n}$ | SECONDARY |
| K | WANTED |
| $\sigma(K)$ | WANTED |

This preliminary procedure is similar to OBTAIN_K1, except now a whole series of samples are prepared which should remove systematic errors in the determination of K. Hence as in OBTAIN_K1 the errors in the intensity ratio are given by:

$$\sigma^2\left(\frac{I(A)}{I(std)}\right) = \left(\frac{1}{I(std)}\right)^2 \sigma^2(I(A)) + \left(\frac{I(A)}{I(std)^2}\right)^2 \sigma^2(I(std))$$

Again, the algorithm uses information in the data base DB2 regarding the phases A and STD to calculate the total diffraction pattern for various weight ratios, determine the intensity ratios and estimate the errors from the above equation. Again, a check for overlapping peaks should be made:

The variation of the intensity ratio for various ($N_n$) weight ratios as a function weight is again given by:

$$I(\text{phase}) \propto \frac{(F_{hkl}(\text{phase}))^2 \frac{W(\text{phase})}{\rho(\text{phase})}}{\sum_{J=1}^{J=n}\left(\frac{W(J)}{\rho(J)}\right)\bar{\mu}}$$

The algorithm calculates various series of intensity ratio combinations for a range of weight ratios and determines $\sigma(K)$ using a suitable least squares best fit approach. This will then produce a list of $\sigma(K)$ versus time, where time should include some factor relating to the intensity of the reflections used, the time to make samples and hence the number of experiments, etc.

Although in the examples described above, the user is requested, in a manner similar to that described above with reference to FIGS. 2 and 3 in relation to the analytical procedure for determining the desired parameter (that is step 44), to select one of these two analytical procedures, if desired, the user and/or computer system could request both of the analytical procedures to be simulated, and then the user can select the most appropriate one from a comparison of the results. Both of these analytical procedures for obtaining K require primary parameters that are available in the data base DB2 and therefore can be simulated.

To summarise, if the user chooses OBTAIN-K1 to obtain K, then a series (~10) of simulated experiments is used to establish a value for K by selecting a series of weight ratios and calculating the intensity ratios for all the appropriate reflections. If on the other hand the user chooses OBTAIN_K2, then the process is somewhat different in that the number of weight ratios used can be varied (between 2 and 10, for example) as well to establish a list of possible experiments to determine K against time (related to the number of experiments with different weight ratios) and $\sigma.(K)$.

The computer system 10 thus uses the selected preliminary analytical procedure OBTAIN_K1 or OBTAIN_K2 to estimate a value for K and the associated error. Although, the computer system may simply use these values to enable the simulation of the selected analytical procedure, the computer system 10 may also generate and display to the user a list of experiments to perform, the time for the experiment (related to intensity, number of scans, etc.,) and the accuracy in the determination of K in a manner similar to that which is used to advise the user of the experiments to carry out to determine the actual desired parameter. The user therefore has the choice of accepting the simulated value for K or of carrying out the suggested experiments to obtain an actual value for K. The reliability of the diffractometer in measuring the intensities clearly will influence the error in K.

Once, a value for K has been supplied, either from the preliminary analytical procedure or as a result of the user carrying out experiments proposed by the preliminary analytical procedure, then all the primary parameters for the selected analytical procedure are available and the simulations can be carried out as discussed above with reference to FIGS. 2 and 3 to select the most appropriate experiment to perform. The experimental variables in this case are the most appropriate weight ratios, the number of experiments and best reflection pairs to obtain the appropriate accuracy in $w_o(A)$ and time. Clearly the user has to make a guess at the likely proportion of A, or some possible proportions (to see whether the experiment chosen changes with w(A) and of course the accuracy $\sigma(w(A))$). Of course, as indicated previously, the analytical procedure will avoid any combination of variables which results in any overlapping peaks.

The diffraction patterns for various weight ratios are then simulated and the areas most sensitive to changes in the weight ratios are determined following steps 49 to 54 in FIG. 2. Thus, by changing the weight proportion from fully reacted to partially reacted (or no reaction to partially reacted), the amplitude or intensity I(A) of the peaks of the diffraction pattern will change. The intensities I(A) for all 2θ will change in proportion, but as some of the intensities I(A) will be larger they will show the greatest difference and will provide the chosen areas for measurement, that is they form the areas most sensitive to the desired parameter. If an intensity I(A) is swamped by a contribution from another component, that I(A) will be excluded. Hence a series of errors in $w_o(A)$ for different experiments (combinations of weight ratios, time of experiment . . . ) can be determined and the user can be advised of the most appropriate experiments to carry out to determine the weight proportion of A. As in the previous examples, the user may simply be provided with instructions to enable him to carry out the appropriate experiments or the computer system may control the diffractometer 20 directly.

In the particular embodiments so far described, the computer system (in step 43 of FIG. 2) advises the user of the possible analytical procedures for determining the desired parameter and the user is requested to select (at step 44) which procedure is to be simulated to provide the experimental choices (steps 45 to 54). Where the data for a number of possible analytical procedures is already available to the computer system in one or more of its data bases, then the computer system may be programmed such that the computer system (and not the user) selects automatically the analytical procedures which it then simulates.

In this modification, after the computer system has identified the possible analytical procedures from the user's parameter input (step 42), the computer system may then select each of these possible analytical procedures in turn so as to carry out the simulation (steps 45 to 53) for each of these possible analytical procedures before requiring the user to select any particular procedure and experiment. Thus, after the computer system has displayed in step 54 an ordered list of possible experiments (in terms of accuracy and/or time required) for these possible procedures, the user may then make his choice of the experiment (and procedure) to be conducted. If the analytical experiment is carried out by the computer system controlling the analytical equipment, the user may not be interested in knowing which analytical procedure is being used. In this case, the computer system need not identify to the user (via the display 2) the analytical procedure which is being selected, simulated and used for the analysis of the material sample. Such a user may merely be interested in having the analytical experiment conducted within a specified time range or ranges and within a specified range of accuracy for the material parameter of interest.

At the user input step 42, the user is asked to input the details of the material sample and its desired parameter(s) which he wishes to determine, i.e. the material details such as previously described with reference to FIG. 2. At this user input step 42 or later, the user may also be asked by the computer system to input additional information such as one or more ranges in the accuracy (sensitivity) of an experiment or analysis and/or the time required for an experiment or analysis. These time and/or accuracy ranges which are input by the user (e.g. in a modified step 42) may then be used by the computer system as part of its criteria in determining which analytical procedures are possible to meet the user's requirements, and so may be used by the computer system to select which analytical procedure or procedures to simulate. The final list of experimental choices presented to the user in step 54 may be ordered in terms of these previously input time and/or accuracy ranges.

It will of course be appreciated that additional information may be added to any of the data bases and that, for example, the computer system may "learn" from previous experiments by adding information concerning the apparatus being used or material samples being investigated to the appropriate data base.

Although the above described examples relate to designing and carrying out experiments for analysing material samples using X-ray radiation, the present invention could be applied to analysis methods using different types of radiation, for example visible, ultra-violet or infra red radiation and to experiments using particle radiation. Also, the present invention may be applied to experiments other than radiation diffraction or scattering experiments, for example to experiments where the sample emits light one type or wavelength range of radiation in response to a different type or wavelength range of radiation, for example the present invention could be applied to fluorescence experiments.

From reading the present disclosure, other modifications and variations will be apparent to persons skilled in the art. Such modifications and variations may involve other features which are already known in the art and which may be used instead of or in addition to features already described herein. Although claims have been formulated in this application to particular combinations of features, it should be understood that the scope of the disclosure of the present application also includes any novel feature or combination of features disclosed herein either explicitly or implicitly, whether or not relating to the same invention as presently claimed in any claim and whether or not it mitigates any or all of the same technical problems as does the presently claimed invention. The applicants hereby give notice that new claims may be formulated to such features and/or combinations of such features during prosecution of the present application or of any further application derived therefrom.

I claim:

1. A method of carrying out an analytical procedure comprising executing the following steps using analytical apparatus having a computer system provided with a data base of analytical procedures for analysing a material sample, in the computer system, requesting, a user to input to the computer system information for identifying at least one desired parameter of the material sample which is of interest to the user, determining from the information input by the user, which of the analytical procedures in the data base may be used to obtain the desired information, simulating at least one analytical procedure selected from the possible analytical procedures to produce a first simulation of radiation leaving the sample, varying at least one desired parameter of interest to the user, simulating the selected analytical procedure again after having varied the influence of the at least one desired parameter to produce a second simulation of radiation leaving the sample, comparing the first and second simulations to determine the area or areas where the difference between the first and second simulations is greatest, and controlling the analytical apparatus to cause an experiment to be carried out using the analytical procedure in the area or areas most sensitive to the at least one desired parameter.

2. A method for designing an experiment for analysing a material sample using radiation, comprising the following steps using a computer system having a data base of analytical procedures for analysing a material sample by causing radiation to be incident on the sample and detecting radiation leaving the sample, and executing the following steps in the computer system, requesting a user to input to the computer system information for identifying at least one desired parameter of the material sample which is of interest to the user, determining from the information input by the user which of the analytical procedures in the data base may be used to obtain the desired information, simulating at least one analytical procedure selected from the possible analytical procedures to produce a first simulation of radiation leaving the sample, varying at least one desired parameter of interest to the user, simulating the selected analytical procedure again after having varied the influence of the at least one desired parameter to produce a second simulation of radiation leaving the sample, and comparing the first and second simulations to determine the area or areas where the difference between the first and second simulations is greatest to enable an experiment to be conducted in the area or areas most sensitive to the at least one desired parameter.

3. A method according to claim 2, wherein the experiment is an X-ray scattering experiment, the first and second simulations are simulations of X-ray scattering patterns and the first and second simulations are compared to determine the area or areas of diffraction space where the difference between the first and second simulations is greatest.

4. A method according to claim 2, in which the computer system advises the user of the area or areas most sensitive to the at least one desired parameter.

5. A method according to claim 2, further comprising executing the following step in the computer system storing the analytical procedures in the data base cross-referenced to keywords and requests the user to input the information for identifying the at least one desired parameter by identifying the relevant keyword or keywords.

6. A method according to claim 2, further comprising executing the following steps in the computer system advising the user of the possible analytical procedures for determining the desired at least one parameter and allowing the user to select which of the possible analytical procedures is to be simulated to produce the first and second simulations.

7. A method according to claim 2, further comprising executing the following step in the computer system requesting the user to supply information to enable the computer system to determine the values of parameters required to produce the first simulation.

8. A method according to claim 2, further comprising executing the following steps in the computer system providing a further data base of known parameters for known elements and material compounds and determining from the data base the values of parameters required to produce the first simulation.

9. A method according to claim 7, further comprising executing the following steps in the computer system when all of the required parameters for producing the first simulation cannot be determined, determining, for each unknown parameter, whether the unknown parameter is a primary parameter whose value must be known or a secondary parameter for which an estimate can be used and, where the unknown parameter is a primary parameter, determining from the data base of analytical procedures any possible analytical procedure for determining the unknown primary and advising the user of the analytical procedure for determining the unknown primary parameter.

10. A method according to claim 7, further comprising executing the following steps in the computer system when all of the required parameters for producing the first simulation cannot be determined, determining for each unknown parameter, whether the unknown parameter is a primary parameter whose value must be known or a secondary parameter for which an estimate can be used and, where the unknown parameter is a primary parameter, determining whether there is any other analytical procedure in the data base which can determine the at least one desired parameter but which does not require the unknown parameter as a primary parameter, advising the user of any such other possible analytical procedure and requesting the user to select a new analytical procedure.

11. A method according to claim 9, further comprising executing the following step in the computer system when an unknown required parameter is a secondary parameter, requesting the user to estimate a value or range for the unknown parameter.

12. A method according to claim 2, further comprising executing the following steps in the computer system providing a data base of instrument profiles for a number of different apparatus for carrying out the experiment, requesting the user to input information for identifying the apparatus to be used, selecting an instrument profile from the data base of instrument profiles using the information supplied by the user and convolving the results of the simulations with the selected instrument profile to determine the effect of the actual apparatus to be used on the experiment.

13. A method according to claim 12, further comprising executing the following steps in the computer system where the user inputs information for more than one apparatus, selecting for each apparatus an instrument profile from the data base of instrument profiles using the information supplied by the user and convolving the results of the simulations with the selected instrument profile for each apparatus and determining the most appropriate apparatus for use in the experiment.

14. Apparatus for carrying out an analytical procedure, the apparatus comprising a radiation source, means for defining the radiation beam from the source, a sample support for enabling the sample to be oriented in a desired manner relative to the beam, means for defining radiation from the sample mounted to the sample support, a radiation detector for detecting the radiation from the sample mounted to the sample support, a computer system provided with a data base of analytical procedures for analysing a material sample, the computer system having means for requesting a user to input to the computer system information for identifying at least one desired parameter of the material sample which is of interest to the user, means for determining from the information input by the user which of the analytical procedures in the data base may be used to obtain the desired information, means for simulating at least one analytical procedure selected from the possible analytical procedures to produce a first simulation of radiation leaving the sample, means for varying at least one desired parameter of interest to the user, means for simulating the selected analytical procedure again after having varied the influence of the at least one desired parameter to produce a second simulation of radiation leaving the sample, means for comparing the first and second simulations to determine the area or areas where the difference between the first and second simulations is greatest and means for controlling the analytical apparatus to cause the analytical procedure to be conducted in the area or areas most sensitive to the at least one desired parameter.

15. Apparatus according to claim 14, wherein the means for defining the radiation beam from the source comprises at least one aperture of variable size and means are provided for enabling the size of the at least one aperture to be varied to meet the requirements of the selected analytical procedure.

16. Apparatus for designing an experiment for analysing a material sample using radiation, the apparatus comprising a computer system having a data base of analytical procedures for analysing a material sample by causing radiation to be incident on the sample and detecting radiation leaving the sample, means for requesting a user to input to the computer system information for identifying at least one desired parameter of the material sample which is of interest to the user, means for determining from the information input by the user which of the analytical procedures in the data base may be used to obtain the desired information, means for simulating at least one analytical procedure selected from the possible analytical procedures to produce a first simulation of radiation leaving the sample, means for varying at least one desired parameter of interest to the user, means for simulating the selected analytical procedure again after having varied the influence of the at least one desired parameter to produce a second simulation of radiation leaving the sample, means for comparing the first and second simulations to determine the area or areas where the difference between the first and second simulations is greatest to enable an experiment to be conducted in the area or areas most sensitive to the at least one desired parameter.

17. Apparatus according to claim 16, in which the computer system comprises means for advising the user of the possible analytical procedures for determining the desired at least one parameter and means for allowing the user to select which analytical procedure is to be simulated to produce the first and second simulations.

18. Apparatus according to claim 16, wherein the computer system stores the analytical procedures in the data base cross-referenced to keywords.

19. Apparatus according to claim 16, wherein the computer system provides a data base of instrument profiles for a number of different apparatus for carrying out the experiment and has means for requesting the user to input information for identifying the apparatus to be used, selecting an instrument profile from the data base of instrument profiles using the information supplied by the user and convolving the results of the simulations with the selected instrument profile to determine the effect of the actual apparatus to be used on the experiment.

20. Apparatus according to claim 16, wherein, where the user inputs information for more than one apparatus, the computer system has means for selecting, for each apparatus an instrument profile from the data base of instrument profiles using the information supplied by the user and for convolving the results of the simulations with the selected instrument profile for each apparatus to determine the most appropriate apparatus for use in the experiment.

* * * * *